United States Patent [19]

Melinyshyn et al.

[11] Patent Number: 4,840,690
[45] Date of Patent: Jun. 20, 1989

[54] METHOD OF CONSTRUCTING A BLOOD FLOW CONDUIT

[75] Inventors: Lev A. Melinyshyn, Mt. Prospect; Jeffrey M. Stupar, Chicago; Edward M. Goldberg, Glencoe, all of Ill.

[73] Assignee: Becton, Dickinson and Company, Franklin Lakes, N.J.

[21] Appl. No.: 166,140

[22] Filed: Mar. 10, 1988

Related U.S. Application Data

[62] Division of Ser. No. 899,624, Aug. 25, 1986, Pat. No. 4,731,055.

[51] Int. Cl.⁴ .................. B29C 65/54; A61M 29/02
[52] U.S. Cl. ............................. 156/242; 156/258; 156/289; 156/296; 156/304.2; 156/304.5; 156/329; 264/213; 264/216; 604/101

[58] Field of Search .............. 156/155, 158, 242, 258, 156/289, 296, 304.2, 304.5, 305, 329; 604/101, 102, 103; 264/213, 214, 216

[56] References Cited

U.S. PATENT DOCUMENTS

| | | | |
|---|---|---|---|
| 2,481,488 | 9/1949 | Auzin | 156/242 |
| 2,690,595 | 10/1954 | Raiche | 156/242 |
| 3,635,504 | 1/1972 | Borden et al. | 156/158 |
| 3,873,391 | 3/1975 | Plauka et al. | 156/258 |
| 4,065,046 | 12/1977 | Roberts et al. | 156/155 |

Primary Examiner—Michael Wityshyn

[57] ABSTRACT

A method of constructing a blood flow conduit provided with external inflatable balloons and having rigid end portions for facilitating insertion into blood vessels and means for detecting pulsatile flow in the conduit and excessive pressure in the balloons.

5 Claims, 3 Drawing Sheets

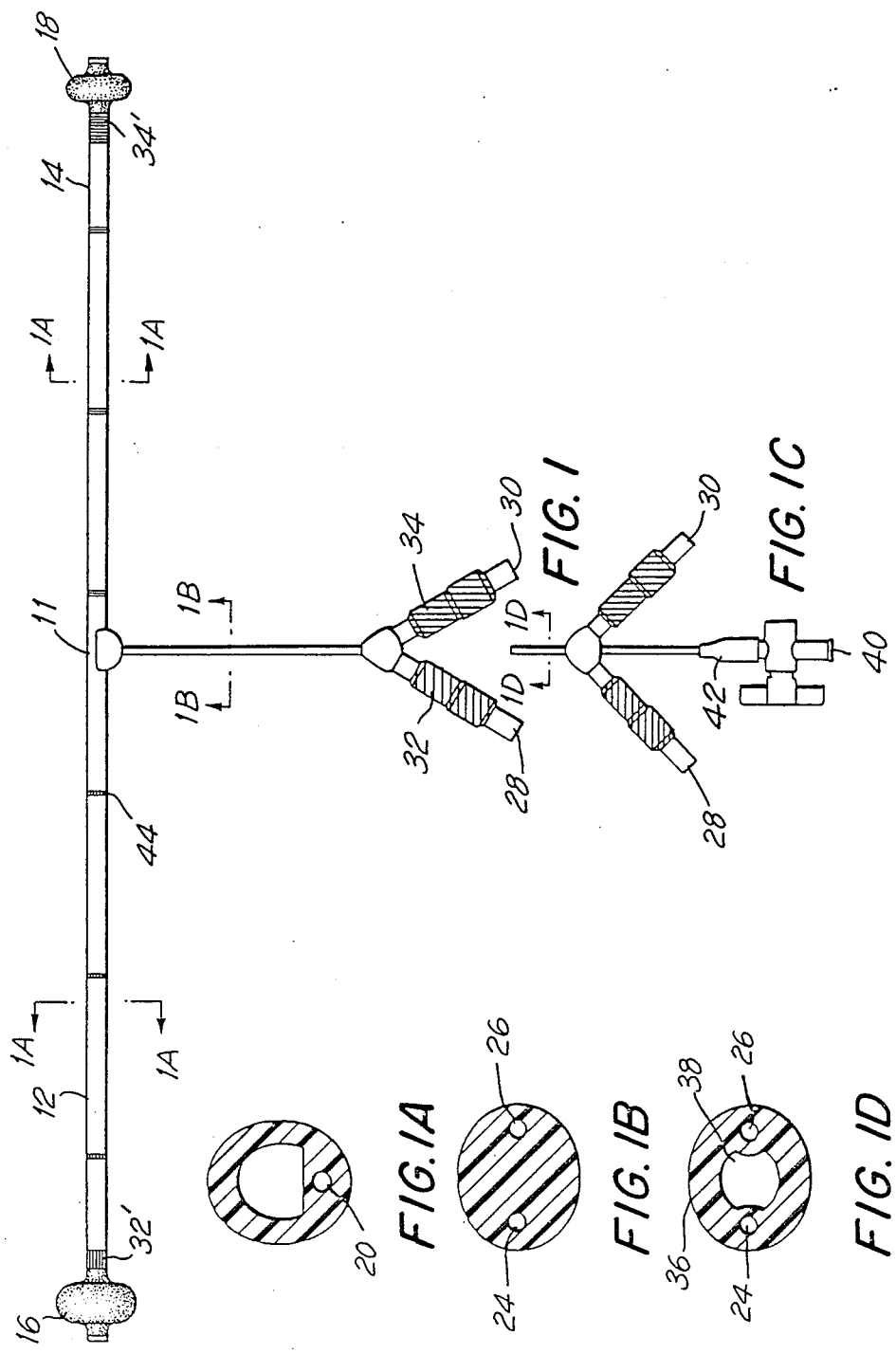

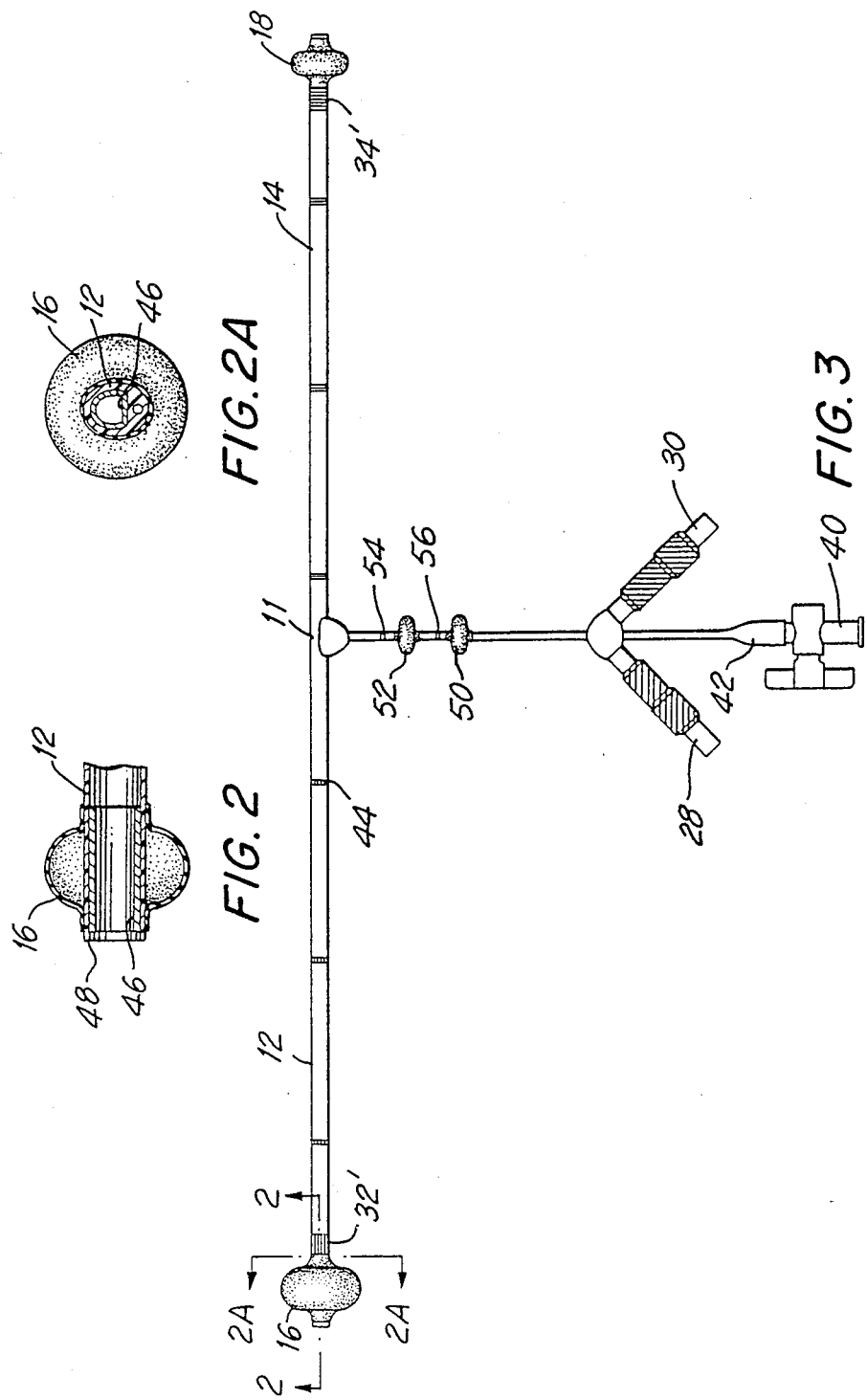

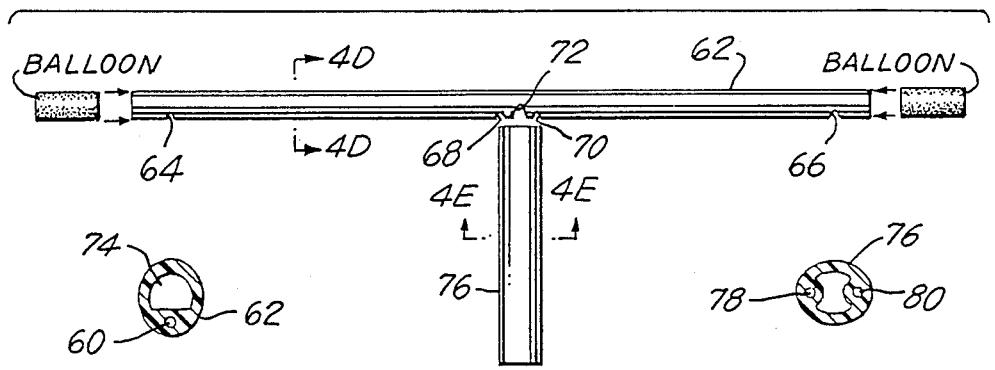
FIG. 4D  FIG. 4A  FIG. 4E
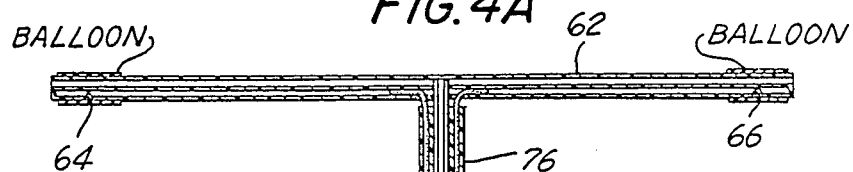
FIG. 4B
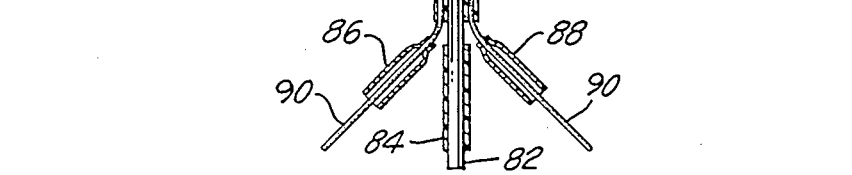
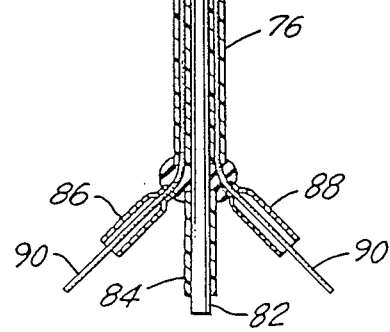
FIG. 4C

METHOD OF CONSTRUCTING A BLOOD FLOW CONDUIT

This is a division of application Ser. No. 899,624, filed Aug. 25, 1986, now U.S. Pat. No. 4,731,055.

BACKGROUND OF THE INVENTION

This invention relates generally to surgical apparatus and the manufacture thereof and, more particularly, to a conduit for transporting blood between blood vessels during surgical procedures without significant blood loss and without the need for potentially damaging and difficult to use clamps or ties for attaching the conduit to the vessels.

Various types of conduits for transporting blood between blood vessels are known. For example, U.S. Pat. No. 3,435,824 describes a surgical apparatus which may be used in by-passing an arterial vessel so that the flow of blood can continue while a diseased section of the vessel is corrected. The apparatus includes a tube with a continuous axially disposed bore and inflatable means encircling the end portions of the tube for maintaining the tube in position within the circulatory system.

An indwelling double balloon shunt for carotid endarterectomy is described in a technical note authored by Furui and Hasuo, which appeared in the *Journal of Neurosurgery*, 60: 861-863, 1984. The shunt described comprises a soft silicone tube equipped with silicone balloons at both ends which are inflated to hold the tube in place during the endarterectomy procedure while preventing bleeding from the gap between the tube and the inner surface of the carotid arteries. Other double balloon shunts are commercially available using a rigid vinyl tube instead of the silicone tube used by Furui and Hasuo.

Both prior rigid and resilient blood flow conduits bearing inflatable balloons at the conduit ends for occluding blood flow between a blood vessel and the outer surface of the tube have significant drawbacks. For example, when the tubes are made of a rigid material such as vinyl, insertion into the blood vessels can cause displacement of arterial plaque and damage to the vessel wall. Furthermore, such rigid tubes may traumatize the blood cells which pass through them. On the other hand, when the more resilient silicone tubes are used, it is sometimes difficult to guide the highly flexible tube ends into the vessel. Also, once the tubes are inserted and the balloons are inflated, the inadvertent application of excess pressure in the balloons may collapse the tube thereby occluding the lumen and blocking or impeding blood flow.

Other potential problems with present blood flow conduits include the difficulty of sensing blood flow in the conduit and the danger of puncturing an inflated balloon with a sharp instrument while performing, for example, an endarterectomy procedure. With particular reference to the endarterectomy procedure, prior art devices generally follow a "one size fits all" philosophy, failing to provide a longer conduit branch for the common carotid which is longer than the internal carotid and typically contains plaque to a greater depth than found in the internal carotid.

Finally, the methods used in manufacturing prior art devices of the present type are generally complex and result in an unduly expensive product.

SUMMARY OF THE INVENTION

It is therefore an object of the present invention to provide an improved blood flow conduit made of silicone or other soft, flexible elastomers which carries inflatable balloons at its ends that may be inflated for intraluminal attachment of the conduit to blood vessels without the need for vessel clamps or ties.

It is yet another object of the present invention to provide a blood flow conduit which is sufficiently resilient along most of its length to minimize trauma to blood cells and to permit clamping of the conduit without damage yet rigid enough near its ends to enable it to be readily inserted in blood vessels.

A further object of the present invention is to provide a blood flow conduit with inflatable balloons at its ends, which is resilient along most of its length yet will not collapse upon application of excessive pressure to the balloons.

Yet another object of the present invention is to provide a blood flow conduit which includes an elongated branch for indwelling intraluminal application to the common carotid artery in performing a carotid endarterectomy.

A still further object of the present invention is to provide a blood flow conduit with pressure sensing means which provide a tactile indication of the pulsatile flow of blood in the conduit.

Another object of the present invention is to provide an improved method for manufacturing a blood flow conduit with balloons at either end which may be inflated for intraluminal attachment to blood vessels.

The present invention is therefore directed to a blood flow conduit including a resilient tube having at least two end portions provided with external inflatable balloons encircling the tube adjacent the end portions and bushings positioned within the resilient tube below the inflatable balloons. In one important embodiment, the invention is directed to a blood flow conduit which includes an longated end with an enlarged balloon which is particularly well adapted for attachment to the common carotid artery. In yet another important alternative embodiment, the invention is directed to a blood flow conduit having end portions provided with external inflatable balloons and means for providing a tactile and visual indication of the pulsatile flow of blood flow in the conduit. In a still further important embodiment, the invention is directed to a blood flow conduit of the type generally described, in which means are provided for tactilely and visually indicating when excessive pressure is applied to the intraluminal balloons.

BRIEF DESCRIPTION OF THE DRAWINGS

The features of this invention which are believed to be novel are set forth with particularity in the appended claims. The invention, together with its objects and advantages thereof, may be best understood by reference to the following description, taken in conjunction with the accompanying drawings, in which like referenced numerals identify like elements in the several figures and in which:

FIG. 1 is a front elevation view of a blood flow conduit in accordance with the present invention;

FIGS. 1A and 1B are cross sectional views, taken on section lines 1A—1A and 1B—1B of FIG. 1, showing in an enlarged cross-sectional view the position of the inflation lumens in the apparatus of the invention;

FIG. 1C is a fragmentary front elevation view of an alternative embodiment of the invention in which the inflation tube of the apparatus of the invention includes a large central lumen in communication with the blood carrying branches of the blood flow conduit of the invention and FIG. 1D is a cross-sectional view of the inflation tube;

FIG. 2 is an alternative of the embodiment of the invention in which a bushing is positioned below the inflatable balloon of the embodiment of FIG. 1 and FIG. 2A is a cross-sectional view thereof taken along section lines 2A—2A;

FIG. 3 is a front elevation view of an alternative embodiment of the invention depicting means for sensing the application of excessive pressure on intraluminal balloons of the device; and FIGS. 4A-C are front elevation views depicting a preferred method of constructing the apparatus of FIGS. 1 and 1C;

FIG. 4D is a cross-sectional view of the blood flow conduit of FIG. 4A taken along line 4D—4D; and FIG. 4E is a cross-sectional view of the blood flow conduit of FIG. 4A taken along line 4E—4E.

DESCRIPTION OF THE PREFERRED EMBODIMENTS

While the invention is described below in connection with one embodiment which is particularly well adapted for use in performing a carotid endarterectomy procedure, the invention is not intended to be limited to this embodiment but rather may be used in any surgical procedure in which a portion of the blood circulatory system must be by-passed while maintaining blood flow therein.

Turning now to FIG. 1, there is illustrated a blood flow conduit 10 constructed in accordance with the present invention, comprising silicone tube 11 including a a common carotid branch 12 and an internal carotid branch 14 with respective common carotid balloon 16 and internal carotid balloon 18 (balloons inflated for illustration purposes). As is shown in exaggerated form for purposes of illustration, common carotid branch 12 and common carotid balloon 16 are enlarged to permit a deeper fit with greater contact area in the common carotid artery in order to more effectively control the escape of blood under the higher blood pressure present in the common carotid artery during the endarterectomy procedure.

Balloons 16 and 18 comprise flexible silicone collars integrally bonded to their respective branches of tube 11 in a conventional fashion using silicone room temperature vulcanizing ("RTV") adhesive. An inflation lumen 20 formed in a conventional extrusion process runs along the wall of tube 11 in each of the conduit branches, as best seen in the cross-sectional view of FIG. 1A.

An inflation tube 22 is joined to the tube 11 at the intersection of branches 12 and 14. Inflation lumens 24 and 26 (FIG. 1B) of the inflation tube communicate with balloons 16 and 18 through their respective portions of inflation lumen 20 and with conventional syringe activated valves 28 and 30 located near the proximal end of the inflation tube. The valves are color-coded, at 32 and 34, to corresponding color bands 32' and 34' adjacent the inner edge of the balloons. Thus, the surgeon can inflate the desired balloon by introducing by way of a syringe a pressure medium such as saline through the appropriate color-coded syringe valve in communication with that balloon. The markings adjacent the balloons also serve to alert the surgeon when he is working in their vicinity to thereby minimize the danger that he will inadvertently puncture a balloon.

In another embodiment of the invention, inflation tube 22 of FIG. 1 may be replaced by an alternate inflation tube 36 having a large central lumen 38 in communication with the blood carrying branches 12 and 14 of tube 11 as illustrated in FIGS. 1C and 1D. Tube 36 is provided with a stopcock 40 which may be affixed to the tube as shown with a shrink bank 42. Tube 36 acts as an access port for the introduction of drugs into the blood flowing in tube 11, for the attachment of devices for continuously monitoring pressure in the system, or for blood sampling.

Branches 12 and 14 of tube 11 have depth markings 44 spaced every five centimeters to give the surgeon an indication of the depth of insertion of the branch in the blood vessel. These depth markings are preferably color coordinated with the band markings 32' and 34' at the balloons to identify the branch with its respective valve and balloon.

Turning now to FIGS. 2 and 2A, there is illustrated an important embodiment of the invention in which a rigid tube 46 is positioned within the lumen of branch 12 to facilitate insertion of the end of the branch into a blood vessel. As is seen best in FIG. 2, the rigid tube is offset from the end of the soft rounded end of the branch leaving a resilient silicone edge 48 to lead the way into vessel with minimal disturbance of arterial plaque and minimal interruption of the vessel wall. This rigid bushing not only aids in the insertion procedure, it also serves the most important role of preventing collapse of the lumen in case excessive pressure is applied to balloon 16. Although illustrated only with respect to branch 12 and balloon 16, the rigid bushing may be applied to the other branch and balloon to achieve like advantages there.

Branches 12 and 14 and inflation tubes 22 or 36 may be constructed of silicone having the proper durometer, wall thickness and lumen diameter to permit a visually and tactilely observable flexure responsive to the pulsatile flow of the blood through tube 11 to visually and tactilely assure the surgeon that blood is flowing as intended. Alternatively, extra resilient sections may be provided in the branches near the point of attachment to tubes 22 or 36 to give more localized such indications.

In yet another embodiment of the invention, illustrated in FIGURE 3, indicator balloons 50 and 52 are affixed to the inflation tube in communication with the inflation lumens corresponding to balloons 16 and 18 to provide a visual and tactile indication to the surgeon of the pressure in the interluminally positioned balloons 16 and 18 as they are being inflated. The indicator balloons may be constructed of a silicone of the proper durometer and thickness such that they begin inflating when the appropriate pressure threshold or maximum desirable pressure of balloons 14 and 18 is exceeded, thereby providing not only an indication of the balloon inflation, but a means of relieving excess intraluminal balloon pressure, diminishing the possibility of resulting vessel damage or bursting of the intraluminal balloons due to over-inflation. Again, it is desirable to provide color coded banding (54 and 56) at each of the indicator balloons to indicate the corresponding intraluminal balloon. Balloons 50 and 52 may alternatively be positioned on the branches 12 and 14 of tube 11.

Turning now to FIGS. 4A, 4B and 4C, a particularly convenient method for construction of the conduit of the present invention is illustrated. The construction uses tubing having an integral inflation lumen 60 along its entire length, constructed by conventional extrusion techniques. A portion of the tubing, 62, is laid out on a glue rack (not shown) and notches 64 and 66 are cut into the tube near either end thereof, above the inflation lumen. Silicone balloons are then affixed over these notches by conventional means such as with the use of silicone RTV adhesive (FIG. 4C).

Offset slightly from the central portion of tube 62, notches 68 and 70 are cut into the wall of tube 62 providing further openings to the inflation lumen. Notches 64–70 are of approximately the same size. Finally, an enlarged opening 72 is cut into tube 62 bisecting the inflation lumen and communicating with the central lumen 74 of tube 62.

Next, another silicone tube 76 having two integral inflation lumens 78 and 80 along its opposite edges is positioned perpendicularly to tube 62, with its distal end opposite opening 72 and with notches 66 and 68 on either side of tube 76, opposite the inflation lumens in the tube. A Teflon (polytetrafluoroethylene) rod 82 is passed through tube 76 so that it protrudes slightly into lumen 74 of tube 62 through opening 72. Next, a section of silicone tubing 84 (without inflation lumens) is passed over the proximale end of the Teflon rod until it abuts the proximal end of tube 76, and funnels 86 and 88 which will be later used to assemble the balloon syringe valves are positioned adjacent the spacing between tubes 76 and 84, with the funnel openings opposite the respective inflation lumens in tube 76.

A nylon filament 90, preferably coated with a silicone release agent, is then threaded through the funnels, into the respective inflation lumens above the funnel tips until the thread reaches notches 68 and 70 where it is passed a short distance into the respective inflation lumens.

A sealing medium such as silicone RTV adhesive is then applied to seal the intersection of tubes 62 and 76 and at funnels 86 and 82 to seal the system, as depicted in FIG. 4C. The adhesive is permitted to cure and then the Teflon rod and filaments are removed leaving open access between the lumens of tubes 62 and 76 and a clear passage between funnels 86 and 88 and the respective inflation lumens of each branch of tube 76.

The funnel balloon inflation ports are then assembled and a stopcock is applied to tube 84 by conventional means such as elastic press fit bushings. In one of the alternative embodiments discussed above, additional notches are made in the stopcock inflation tube to accommodate balloons for providing a tactile and visual indication of when excessive pressure is applied to intraluminal balloons 16 and 18. In another of the alternative embodiments discussed above, rigid bushings are slipped into place below balloons 16 and 18 by lubricating the bushings with, e.g., a 50:50 mixture of isopropyl alcohol and water and then forcing them into place. Preferably, the bushing is slipped back a short distance from the edge of the tube to leave a leading edge of the resilient tube to minimize disruption of a vessel upon insertion of the branch.

The blood flow conduit described above may be used in performing a carotid endarterectomy as follows:

1. Purge balloons of air by attaching a syringe containing saline to valves 28 and 30. With the syringe in an upright position and the balloon at the lower end, the plunger is withdrawn to create a vacuum, thus removing any air in the device and eliminating the possibility of an air embolism. Purging is complete when air has ceased to bubble into the saline filled syringe. At that point, the syringe plunger is released allowing the balloon lumen to be filled with saline, and the syringe to be removed and replaced with a smaller syringe.

2. The internal carotid artery is then clamped followed by the clamping of the common and external carotid arteries. A arteriotomy is then performed by standard surgical practice, and the common branch 12 of the conduit is inserted into the common carotid artery. The markings 40 on the common branch are used to gauge the distance of insertion.

3. The common carotid balloon is then inflated by injecting sterile isotonic saline into the corresponding color coded valve until the balloon has reached the required diameter to seal against the inner surface of the vessel whereupon the valve is sealed by removing the syringe therefrom.

4. The clamp occluding the common carotid artery is momentarily released and a small amount of blood is permitted to pass through the conduit to flush out any artheromatous debris that may have been dislodged from the vessel wall upon insertion. A clamp is then applied to partially occlude the internal branch of the conduit to achieve a constant drip whereupon the internal side of the conduit is packed into the non-diseased portion of the internal carotid artery and the clamp is removed.

5. The clamp occluding the internal carotid artery is then released to allow back bleeding, the internal side of the conduit is advanced to the desired position and the internal carotid balloon is inflated by injecting sterile isotonic saline into the corresponding color coded valve until bleeding stops.

6. When a conduit is used which has an access port with a stopcock the system may be accessed via the stopcock. Connection to the stopcock may be made using a luer attachment in the stopcock. This port may be used to withdraw blood samples, perform continuous pressure monitoring, introduce heparized saline, etc.

While the present invention has been described in connection with the use of silicone tubing and silicone balloons, other elastomeric materials may be used in lieu of silicone such as latex, urethane and other thermoplastic elastomers. Also, while the invention is described in connection with an apparatus having two blood carrying branches, devices with more than two branches for interconnection to more than two vessels may be constructed and used in accordance with the present invention.

While particular embodiments of the invention have been shown and described, it will be obvious to those skilled in the art that various changes and modifications may be made therein without departing from the spirit and scope of the invention and, therefore, it is intended in the appended claims to cover all such changes and modifications which fall within the true spirit and scope of the invention.

What is claimed is:

1. A method of constructing a blood flow conduit from a first resilient tube having a central lumen and a first inflation lumen along its inner surface, and a second resilient tube having a central lumen and two second inflation lumens along its inner surface, comprising:

forming first balloon inflation openings in the wall of said first resilient tube adjacent to its ends and in communication with said first inflation lumen;

positioning balloon collars adjacent to the ends of said first tube over said first balloon inflation openings and sealing the edges of said collars to said first tube;

forming a receiving opening passing through the wall of said first tube and, on either side of said receiving opening forming second balloon inflation openings in the wall of said first resilient tube in communication with said first inflation lumen;

positioning said second tube opposite said receiving opening with said second inflation lumens opposite said second balloon inflation openings;

forming third balloon inflation openings in the wall of said second resilient tube in communication with each of its second inflation lumens and positioning inflation means for facilitating connection with an external source of pressured fluid for expanding said balloon collars when said blood flow conduit is being used in a surgical procedure adjacent to each of said third balloon inflation openings;

passing a first thread through one of said inflation means and its corresponding third balloon inflation opening, second inflation lumen, second balloon inflation opening and into the corresponding section of said first inflation lumen;

passing a second thread through the other of said inflation means and its corresponding third balloon inflation opening, second inflation lumen, second balloon inflation opening and into the corresponding section of said first inflation lumen;

sealing said inflation means to the second tube and the intersection of the second tube to the first tube with a sealing medium; and permitting said sealing medium to cure and then removing said first thread and said second thread.

2. The method of claim 1 wherein said first thread and said second thread are nylon.

3. The method of claim 1 wherein a rod is positioned in said central lumen of said second tube, so that it protrudes into said receiving opening before application of the sealing medium, said rod being removed after the curing of said sealing medium.

4. The method of claim 1 wherein said first tube and said second tube are constructed of silicone and said sealing medium is a silicone RTV adhesive.

5. The method of claim 1 wherein said first thread and said second thread are coated with a release agent.

* * * * *